United States Patent [19]

Boehringer et al.

[11] Patent Number: 5,521,102

[45] Date of Patent: May 28, 1996

[54] CONTROLLED SENSITIVITY IMMUNOCHROMATOGRAPHIC ASSAY

[75] Inventors: Hans R. Boehringer; Jan L. Sabran, both of San Diego; Ya-Chen Hsu, Encinitas; Bentley Tam, San Diego, all of Calif.

[73] Assignee: Quidel Corporation, San Diego, Calif.

[21] Appl. No.: 287,179

[22] Filed: Aug. 8, 1994

[51] Int. Cl.⁶ .................................................. G01N 33/543
[52] U.S. Cl. ........................... 436/523; 435/7.1; 435/962; 435/967; 435/970; 436/518; 436/514; 436/525; 436/533; 436/66; 436/810; 436/824; 436/825; 422/56; 422/58; 422/60; 422/61; 422/101
[58] Field of Search ..................... 435/7.1, 7.92, 435/962, 967, 970; 436/518, 514, 523, 525, 533, 66, 810, 824, 825; 422/56, 58, 60, 61, 101

[56] References Cited

U.S. PATENT DOCUMENTS

| | | | |
|---|---|---|---|
| 4,703,017 | 10/1987 | Campbell et al. | 436/501 |
| 5,028,535 | 7/1991 | Buechler et al. | 435/7.1 |
| 5,075,078 | 12/1991 | Osikowicz et al. | 422/56 |
| 5,089,391 | 2/1992 | Buechler et al. | 435/7.1 |
| 5,120,643 | 6/1992 | Ching et al. | 435/7.92 |
| 5,171,528 | 12/1992 | Wardlaw et al. | 422/56 |
| 5,223,220 | 6/1993 | Fan et al. | 422/58 |
| 5,238,847 | 8/1993 | Steinbiss et al. | 436/64 |
| 5,266,497 | 11/1993 | Imai et al. | 436/514 |
| 5,354,692 | 10/1994 | Yang et al. | 436/514 |

*Primary Examiner*—Carol A. Spiegel
*Attorney, Agent, or Firm*—Knobbe, Martens, Olson & Bear

[57] ABSTRACT

An improved one-step immunochromatographic assay which involves the binding of a predetermined amount of analyte to an antibody, enabling the control of the assay sensitivity, is disclosed. The system is especially useful as a controlled sensitivity fecal occult blood assay. Antibodies to a desired analyte, present at a predetermined concentration, are deposited on the sample pad of the reaction unit. The antibody binds analyte present in the sample, up to a threshold amount. Analyte which is present in the sample at a level above the threshold amount proceeds unbound through the sample pad and onto a membrane, where it reacts with an antibody-coated latex and a second, immobilized antibody to generate a positive signal.

29 Claims, No Drawings

CONTROLLED SENSITIVITY IMMUNOCHROMATOGRAPHIC ASSAY

FIELD OF THE INVENTION

The present invention relates to an improved one-step immunochromatographic assay which involves the binding of a predetermined amount of analyte as the first step in assaying for the presence of the analyte, thus allowing for the control of the assay sensitivity. The system is useful, for example, as a controlled sensitivity fecal occult blood assay.

BACKGROUND OF THE INVENTION

Recent technologic advances have made it possible to tailor assays for a wide variety of analytes, especially those molecules exhibiting antigenic characteristics. In general, most assays currently in use tend to use antibodies to bind antigenic substances in a liquid-phase or a solid-phase format. Recently, "one-step" immunoassays have been developed, which are used in the detection of a variety of analytes.

One-step immunochromatographic assays involve the use of colored or other visible particles. For example, a sample is applied to a substrate of absorbent material, and analyte binds to antibody bearing mobile colored latex particles. The particles to which the analyte binds are then themselves bound by immobilized immunoreagent as the sample chromatographically traverses the length of the absorbent material.

Assay sensitivity is defined as the minimum amount of analyte that can be measured with acceptable precision. One area where assay sensitivity is particularly problematic is in the assay of fecal matter to detect the presence of occult blood. A small amount of blood is normally present in human stool samples. Increased amounts of blood in the stool are indicative of pathological bleeding. Currently available assays are not sensitive enough to detect abnormal amounts of fecal occult blood until the level reaches about 1 mg hemoglobin/g feces. Lesser quantities of blood in the stool, however, are indicative of abnormal bleeding. Thus, currently available assays for fecal occult blood are not sensitive enough to detect the presence of abnormally high levels of blood in the stool. However, the sensitivity of any assay for fecal occult blood should not be increased to the point where normal levels of blood in the stool give a positive test result.

There is therefore a need for a simple, accurate, reproducible assay for the detection of analytes such as fecal occult blood, which provides controlled, predetermined assay sensitivity.

SUMMARY OF THE INVENTION

The improved immunochromatographic assay of the present invention involves the binding of a predetermined amount of analyte to an antibody, enabling the control of assay sensitivity. The present invention is useful in assays where signal generation is obtained through the use of particle migration through a membrane, and is particularly useful as a controlled sensitivity fecal occult blood assay.

In accordance with one aspect of the present invention, there is provided an analytical device having controlled sensitivity for the detection of the presence of an analyte in a sample. The device comprises a wicking material having a plurality of substantially planar zones adjacent one another and in absorbent contact with one another, a sample application pad comprising a predetermined amount of a first antibody against the analyte applied to the sample pad prior to application of the sample, a conjugate zone comprising a second antibody to the analyte bound to mobile particles, and a detection zone comprising a third antibody to the analyte immobilized on the wicking material. When a liquid sample containing analyte is applied to the sample pad, a threshold amount of the analyte is bound to the first antibody, and the analyte remaining unbound in the sample passes from the sample pad through the conjugate zone where it is bound to the second antibody, and through the detection zone where it is bound to the third antibody and immobilized.

The mobile particles are preferably colored latex particles or a metal sol, and more preferably, are colored latex particles. The wicking material is preferably nitrocellulose, and the first and second antibodies are preferably monoclonal. In a preferred embodiment, the second antibody is the same antibody as the first antibody. In another preferred embodiment, the first antibody is polyclonal. In yet another preferred embodiment, the third antibody is the same antibody as the first antibody.

In still another preferred embodiment, the conjugate zone further comprises an antigen conjugated to mobile particles, and the device further comprises a test complete zone comprising a fourth antibody against the antigen. Preferably, the antigen is goat serum albumin. In another preferred embodiment, the device of the present invention further comprises a negative signal comprising visually detectable particles immobilized on the membrane in the detection zone. The particles are preferably immobilized on the membrane in a horizontal line, and the third antibody is immobilized on the membrane in a vertical line which crosses the horizontal line.

In accordance with another aspect of the present invention, there is provided a method for the detection of an analyte in a sample using a device which comprises a wicking material having a plurality of substantially planar zones adjacent one another and in absorbent contact with one another, a sample application pad comprising a predetermined amount of a first antibody to the analyte applied to the sample pad prior to application of the sample, a conjugate zone comprising a second antibody to the analyte bound to mobile particles, and a detection zone comprising a third antibody to the analyte immobilized on the wicking material, When a liquid sample containing analyte is applied to the sample pad, a threshold amount of the analyte is bound to the first antibody, and the analyte remaining unbound in the sample passes from the sample pad through the conjugate zone where it is bound to the second antibody, and through the detection zone where it is bound to the third antibody and immobilized. The method of the present invention comprises applying a liquid sample to the sample pad of the device, waiting a sufficient time to allow the sample to traverse the sample pad, the conjugate zone and the detection zone, and determining the presence or absence of the analyte in the sample based on the appearance of the detection zone.

In accordance with yet another aspect of the present invention, in a one-step immunochromatographic assay for the detection of the presence of an analyte in a sample involving the interaction of antigens and antibodies on a support layer, wherein one of the reagents used in the assay comprises a first mobile particle to which a first antibody against the analyte is bound, and another reagent comprises a second antibody against the analyte immobilized in a first defined zone on the support layer, there is provided the improvement comprising contacting the sample with a predetermined amount of an antibody to the analyte prior to contacting the sample with the first and second antibodies, the antibody being applied onto a second defined zone on the support layer prior to application of the sample.

In accordance with still another aspect of the present invention, there is provided an analytical device having controlled sensitivity for the detection of the presence of blood in a sample of human feces, comprising a wicking material having a plurality of substantially planar zones adjacent one another and in absorbent contact with one another, a sample application pad comprising a predetermined amount of a first antibody to human hemoglobin applied onto the sample pad prior to application of the sample, a conjugate zone comprising a second antibody to human hemoglobin bound to mobile particles, and a detection zone comprising a third antibody to human hemoglobin immobilized on the wicking material. When a sample of feces containing hemoglobin is suspended in a buffer and applied to the sample pad, a threshold amount of the hemoglobin is bound to the first antibody, and the hemoglobin remaining unbound in the sample passes from the sample pad through the conjugate zone where it is bound to the second antibody, and through the detection zone where it is bound to the third antibody and immobilized, producing a detectable signal.

The mobile particles are preferably colored latex particles or a metal sol, and more preferably, are colored latex particles. The wicking material is preferably nitrocellulose. The first and second antibodies are preferably monoclonal. In a preferred embodiment, the second antibody is the same as the first antibody. In another preferred embodiment, the first antibody is polyclonal. In yet another preferred embodiment, the third antibody is the same as the first antibody.

In another preferred embodiment, the conjugate zone further comprises an antigen conjugated to mobile particles, and the device further comprises a test complete zone comprising a fourth antibody against the antigen. The antigen is preferably goat serum albumin.

In still another preferred embodiment, the device of the present invention further comprises a negative signal comprising visually detectable particles immobilized on the membrane in the detection zone. The particles are preferably immobilized on the membrane in a horizontal line, and the third antibody is preferably immobilized on the membrane in a vertical line which crosses the horizontal line.

In accordance with yet another aspect of the present invention, there is provided a method for the detection of blood in a sample of feces, using a device which comprises a wicking material having a plurality of substantially planar zones adjacent one another and in absorbent contact with one another, a sample application pad comprising a predetermined amount of a first antibody to human hemoglobin applied onto the sample pad prior to application of the sample, a conjugate zone comprising a second antibody to human hemoglobin bound to mobile particles, and a detection zone comprising a third antibody to human hemoglobin immobilized on the wicking material. When a sample of feces containing hemoglobin is suspended in a buffer and applied to the sample pad, a threshold amount of the hemoglobin is bound to the first antibody, and the hemoglobin remaining unbound in the sample passes from the sample pad through the conjugate zone where it is bound to the second antibody, and through the detection zone where it is bound to the third antibody and immobilized, producing a detectable signal. The method comprises suspending the sample of feces into a buffer, applying the buffer containing the sample of feces to the sample pad of the device, waiting a sufficient time to allow the buffer to traverse the sample pad, the conjugate zone and the detection zone, and determining the presence or absence of hemoglobin in the sample based on the appearance of the detection zone.

DETAILED DESCRIPTION

We have discovered an improved one-step immunochromatographic assay having adjustable analytic sensitivity. The improvement is especially applicable in immunochromatographic assays of the type disclosed in U.S. Pat. Nos. 5,096,837 and 5,223,220 to Fan et al., the disclosures of which are hereby incorporated by reference. The improvement, however, is applicable to all assays in which signal generation is obtained with the use of horizontal particle migration through a membrane.

A. Preparation of Antibody-Latex Conjugates

Uniform latex particles ("ULPs") are, in general, extremely uniform spheres of small diameter. Typical diameters range from less than about 0.1 μm to about 100 μm. Particles smaller than 5 μm are usually prepared by emulsion polymerization.

The basic process of protein-latex conjugation, for example, via simple adsorption or covalent binding, is well known in the art, as is the use of colored latex particles, which increase the resolution and readability of assays. Various conjugation procedures are described in general terms in Bangs, L. B., "Uniform Latex Particles," presented at a workshop at the 41st National Meeting, Amer. Assoc. Clin. Chem., 1989, and available in printed form from Seragen Diagnostics Inc., Indianapolis, Ind.; or Galloway, R. J., "Development of Microparticle Tests and Immunoassays," Seradyn, Inc., Indianapolis, Ind. These articles, and references cited to therein, are hereby incorporated by reference.

One method of preparing coated latex particles, for example, is the adsorption method. In general terms, one should: 1) utilize pure reagents; 2) clean the particles prior to coating; and 3) determine the quantitative surface coverage of the particle and the ligand chemistry.

For example, antibody-latex conjugates ("Ab-latex") may be prepared according to the following method: in the simplest case, the appropriate ligand is dissolved in a buffer solution, added to a latex suspension, and stirred for times ranging from a few minutes to more than 24 hours. After equilibration, the latex is centrifuged and the supernatant containing any unadsorbed ligand is discarded. The latex is re-suspended in fresh buffer and centrifuged; the supernatant is again discarded. These steps are to be repeated until the latex is determined to be washed free of any residual un-adsorbed ligand. At this juncture, the latex coating process may be complete and the latex ready to use in latex agglutination assays.

Covalent coupling involves the permanent or covalent binding of a ligand or other material to the latex particle surface. If covalent coupling is the method of choice, one must first couple the ligand to the latex particles, then maintain the stability of the latex particle suspension, and then prevent the protein from becoming denatured. (For a general discussion of covalent coupling techniques, and citation to more detailed references, see Bangs, L. B., "Uniform Latex Particles," which is incorporated herein by reference.)

While the foregoing discussion is in the context of latex particles, it will be appreciated that other particles, including, without limitation, other synthetic particles and metal colloids or particles (e.g., gold sol particles), can be used. These particles and their methods of preparation are well known in the art.

B. Preparation of BSA-Latex Conjugates

Preparation of bovine serum albumin-latex conjugates ("BSA-latex") is similar to antibody-latex (Ab-latex) preparation, as described above, except that BSA is used instead. Alternatively, other proteins may be used in place of the BSA, such as other albumins including lactalbumin, casein, globulin, non-specific immunoglobulin (which does not participate in the antigen-antibody reaction), and the like that can prevent nonspecific binding.

C. Preparation of GSA-Latex Conjugates

Preparation of goat serum albumin-latex conjugates ("GSA-latex") is similar to BSA-latex preparation described above, except that GSA is used in place of BSA. Again, other proteins may be used in place of the goat serum albumin, which is used as a means of generating a "test complete" signal, or positive procedural control signal, as will be described below in detail.

D. Mixture of Conjugates

Ab-latex, BSA-latex and GSA-latex are mixed together in varying ratios, depending upon the test to be performed. Depending upon the nature of the assay, the ratios can vary substantially, with greater amounts of albumin-labeled latex resulting in greater reduction of nonspecific binding. The amount of latex that does not have antibody attached can be any amount that is effective to appreciably decrease nonspecific binding, or false positives. Such amounts are readily determined by obvious empirical methods.

E. One-Step Assay Procedure

1. Preparation of One-Step Reaction Unit

One example of the use of the present invention in a solid phase assay format may proceed essentially as follows. The reaction device consists of a solid, typically plastic, housing containing a solid support for the assay. The solid support is preferably comprised of a wicking material which draws liquid. Preferably, a membrane strip such as nitrocellulose is used. The membrane preferably comprises a strip of nitrocellulose membrane having a pore size of about 8µ, albeit larger or smaller pore sizes may be used. A pore size ranging from about 3µ to about 12µ is preferred.

The right end of the membrane is in contact with the sample well. The sample well contains an absorbent pad which provides an even flow of the sample fluid from right to left along the membrane. Alternatively, the reaction unit can be assembled such that the sample flow is from left to right, or in any other orientation across the membrane.

To allow for the control of the sensitivity of the assay, monoclonal or polyclonal antibodies or fragments thereof specific for the test analyte are deposited in a buffer onto the sample pad and allowed to dry. When sample containing the analyte is added to the sample pad, the antibody deposited on the pad will bind some of the analyte. Excess analyte which does not bind to the antibody proceeds through the sample pad and onto the membrane, to react with antibody-coated mobile colored latex particles deposited on the membrane. By varying the amount of antibody applied to the sample pad, a baseline or threshold level of analyte is set. Analyte present in the sample in an amount above this threshold level proceeds unbound through the sample pad and onto the membrane to give a positive result. Analyte present in the sample in an amount less than the threshold level will be bound to antibody and will not react with the antibody-coated mobile colored latex particles, and a negative result will follow. This allows the sensitivity of the assay to be predetermined during manufacture of the reaction device.

Mobile particles, such as colored latex particles, are applied to a first zone of the membrane, the conjugate zone. These particles are conjugated with an appropriate antibody which binds the desired analyte, and can be the same antibody as that applied to the sample pad. This zone can also contain conjugates of BSA-latex which reduce non-specific binding, and GSA-latex, which acts as a positive procedural control.

In a second zone on the membrane, the detection zone, a second antibody is immobilized. This antibody is also directed against the analyte, and can be polyclonal or monoclonal. If analyte is present in the sample above the threshold level, the antibody in the second zone will bind to the analyte, which is bound to antibody conjugated to the mobile colored latex particle. The result is a visually detectable antibody-antigen-antibody conjugate "sandwich" immobilized in the second zone on the membrane.

Also in the second zone, there is preferably an immobilized "negative" signal, generally in the form of a horizontal line. This line is preferably comprised of visually detectable particles, such as colored latex particles, immobilized on the membrane. Preferably, the second antibody described above is immobilized on the membrane in a vertical line which crosses the negative signal. Thus, when analyte is not present in the sample in an amount greater than the threshold level, only the horizontal negative signal is visible. When the analyte is present in an amount above the threshold level, the analyte-antibody conjugate is bound to the second antibody, resulting in a positive or "+" signal appearing on the membrane.

A third reagent may be used as well, preferably deposited in a third zone, the test complete zone, on the membrane. This reagent is capable of binding particles that migrate from the first zone after sample is added. This third agent can act as a procedural control and serve to indicate that the assay is complete, or that it has been properly performed, if, for example, a detectable response occurs in the zone in which the third agent is immobilized. This third agent comprises an antibody which binds the antigen-latex conjugate, such as the GSA-latex conjugate.

In the chromatographic assay test procedure of the present invention, a liquid specimen is applied to the solid support proximal to the first zone. As described above, a predetermined amount of antigen present in the sample is bound to antibody present on the sample pad. As the fluid moves via capillary action to the first zone of the membrane, it mobilizes the latex particles having antibodies or proteins conjugated to the particles. Antigen present in the sample above the threshold level binds to the antibody on the latex particles. The fluid then continues to move the particles across the membrane to the next zone or zones. If analyte is present in the sample above the threshold level, a "sandwich" of immobilized antibody/analyte/antibody-conjugated particles is formed and a detectable result occurs. As the fluid continues to move the particles across the membrane, the fluid and particles come into contact with and bind with the third reagent, which is immobilized on the membrane. A detectable response should then occur in that zone, indicating that the test is valid, or that the test is complete.

The invention can be better understood by way of the following examples which are representative of the preferred embodiments, but which are not to be construed as limiting the scope of the invention.

EXAMPLE I

Preparation of Fecal Occult Blood Reaction Unit

The assay reaction unit utilized in one embodiment of the present invention comprises a 1 cm×5 cm strip of nitrocellulose with a pore size of 8μ housed in a plastic casing. To an absorbent sample pad was added 40 μL of a capture solution. The capture solution comprised 150–200 μg/mL monoclonal anti-human hemoglobin (anti-h Hb), 5 mg/mL affinity-purified rabbit IgG, 2% casein, 5% Zwittergent (CalBiochem, La Jolla, Calif.) 0.22M Tris (Sigma Co., St. Louis, Mo.) and 0.01 mg/mL fluorescein, at a pH of 8.2. The capture solution was deposited onto the sample pad of the reaction unit and allowed to dry.

Approximately 3 μL (2.0–3.4 mg) of a latex anti-human hemoglobin coating solution was applied to a first zone of the membrane. The coating solution comprised 0.15–0.25% monoclonal anti-human hemoglobin conjugated to approximately 0.30–0.34 μm blue latex particles, 0.5% goat serum albumin-blue latex conjugate, and bovine serum albumin-white latex conjugate in an amount sufficient to bring the total latex concentration of the coating solution to 1.7%.

Approximately 0.5 μL of a positive line coating solution was applied to a second zone of the membrane in a vertical line. The coating solution comprised 4 mg/ml Affinity purified rabbit anti-human hemoglobin and 0.01 mg/mL fluorescein in PBS/NaN$_3$, at a pH of 7.7.

Also in this second zone, a negative signal was created by applying 0.5 μL of a negative latex solution on the membrane in a horizontal line. The negative latex solution comprised 0.75% blue latex and 0.2% PEG in 40 mM borate, at a pH of 8.5.

The "test complete" signal was created in a third zone on the membrane. 0.5 μL of a solution comprising 0.5 mg/mL affinity purified rabbit anti-goat albumin antibody in PBS/NaN$_3$ was deposited on the membrane at a third location.

To assemble the reaction unit, the membrane was placed in the plastic housing. The housing contained a sample addition well, as well as openings or windows through which the membrane was visible. The membrane was placed inside the housing such that the sample pad was below the sample addition well, one end of the membrane was in contact with the sample pad, and the second and third zones of the membrane were visible through the windows in the plastic casing.

EXAMPLE II

One-Step Fecal Occult Blood Assay Procedure

Amounts of human hemoglobin ranging from 0.0 to 25.0 mg/g were added to human feces. As a control for specificity of the assay, 1.0 mg/g bovine hemoglobin was added to human feces. Approximately 12 mg of each sample of fecal material containing hemoglobin was placed in a tube containing 1.25 mL transport buffer. The transport buffer contained 1.0% protease-free BSA, 2mM EDTA, 50 mM Tris (Sigma Co., St. Louis, Mo.), 0.88% NaCl, 0.037% formaldehyde, 0.1% Proclin 300 (a preservative comprising 5-chloro-2-methyl-4-isothiazolin-3one, 2-methyl-4-isothiazolin-3-one, modified glycol and alkylcarboxylate) (Rohm-Haas, Philadelphia, Pa.), and 0.1% NaN$_3$, at a pH of 8.8. Each tube was closed and shaken 10–15 times to suspend the fecal matter in the buffer.

Approximately 200–250 μL of the buffer containing the fecal matter was added to the sample pad of the one-step reaction unit described in Example I. The test results were read at 10 minutes, 30 minutes, and 60 minutes after addition of sample to the reaction unit. The signal generated was designated as either negative or positive: a result was judged negative when only the preprinted blue horizontal line was visible in the second zone on the membrane; a result was judged positive when a blue color was visible in a vertical line in the second zone on the membrane. Each of the samples were tested using 3 different manufacturing lots of the reaction units of the present invention.

Each sample was also tested using Hemoccult® SENSA® (SmithKline Diagnostics, Sunnyvale, Calif.), and OC-Hemodia® (Eiken, Japan) according to manufacturer's instructions. The results of the assays are shown in Tables 1–3. The abbreviations used in the Tables are: "CARDS®", for the registered trademark of the device of the present invention, "O.S.®" for one-step, "FOBT" for fecal occult blood test, "SKD" for SmithKline Diagnostics, "Hb" for hemoglobin and "bov." for bovine. The columns in Tables 1–3 labeled with "CARDS® O.S.® FOBT" refer to the results obtained with the present invention.

TABLE 1

Interpretation of CARDS ® O.S. ® FOBT, SKD Hemoccult ® SENSA ®, and Eiken OC-Hemodia ®

| mg Hb/g feces | CARDS ® O.S. ® FOBT (Lot #B01032) | | | SKD Hemoccult ® SENSA ® | Eiken OC-Hemodia ® |
| --- | --- | --- | --- | --- | --- |
| | 10 min. reading | 30 min. reading | 60 min. reading | | |
| 0.000 | Negative | Negative | Negative | Negative | Negative |
| 0.005 | Negative | Negative | Negative | Negative | Negative |
| 0.010 | Negative | Negative | Negative | Negative | Negative |
| 0.050 | Negative | Pos/Neg* | Pos/Neg* | Negative | Positive |
| 0.100 | Negative | Positive | Positive | Negative | Positive |
| 0.200 | Positive | Positive | Positive | Negative | Positive |
| 0.500 | Positive | Positive | Positive | Negative | Positive |
| 1.000 | Positive | Positive | Positive | Positive | Positive |
| 2.500 | Positive | Positive | Positive | Positive | Positive |

TABLE 1-continued

Interpretation of CARDS ® O.S. ® FOBT,
SKD Hemoccult ® SENSA ®, and Eiken OC-Hemodia ®

| mg Hb/g feces | CARDS ® O.S. ® FOBT (Lot #B01032) | | | SKD Hemoccult ® SENSA ® | Eiken OC-Hemodia ® |
|---|---|---|---|---|---|
| | 10 min. reading | 30 min. reading | 60 min. reading | | |
| 5.000 | Positive | Positive | Positive | Positive | Positive |
| 10.000 | Positive | Positive | Positive | Positive | Positive |
| 25.000 | Positive | Positive | Positive | Positive | Positive |
| 1.0 mg bov. Hb/g | Negative | Negative | Negative | Positive | Negative |

*One out of three reaction units was positive; two out of three reaction units were negative.

TABLE 2

Interpretation of CARDS ® O.S. ® FOBT,
SKD Hemoccult ® SENSA ®, and Eiken OC-Hemodia ®

| mg Hb/g feces | CARDS ® O.S. ® FOBT (Lot #B02001) | | | SKD Hemoccult ® SENSA ® | Eiken OC-Hemodia ® |
|---|---|---|---|---|---|
| | 10 min. reading | 30 min. reading | 60 min. reading | | |
| 0.000 | Negative | Negative | Negative | Negative | Negative |
| 0.005 | Negative | Negative | Negative | Negative | Negative |
| 0.010 | Negative | Negative | Negative | Negative | Negative |
| 0.050 | Negative | Positive | Positive | Negative | Positive |
| 0.100 | Positive | Positive | Positive | Negative | Positive |
| 0.200 | Positive | Positive | Positive | Negative | Positive |
| 0.500 | Positive | Positive | Positive | Negative | Positive |
| 1.000 | Positive | Positive | Positive | Positive | Positive |
| 2.500 | Positive | Positive | Positive | Positive | Positive |
| 5.000 | Positive | Positive | Positive | Positive | Positive |
| 10.000 | Positive | Positive | Positive | Positive | Positive |
| 25.000 | Positive | Positive | Positive | Positive | Positive |
| 1.0 mg bov. Hb/g | Negative | Negative | Negative | Positive | Negative |

TABLE 3

Interpretation of CARDS ® O.S. ® FOBT,
SKD Hemoccult ® SENSA ®, and Eiken OC-Hemodia ®

| mg Hb/g feces | CARDS ® O.S. ® FOBT (Lot #B04056.2) | | | SKD Hemoccult ® SENSA ® | Eiken OC-Hemodia ® |
|---|---|---|---|---|---|
| | 10 min. reading | 30 min. reading | 60 min. reading | | |
| 0.000 | Negative | Negative | Negative | Negative | Negative |
| 0.005 | Negative | Negative | Negative | Negative | n.t. |
| 0.010 | Negative | Negative | Negative | Negative | Negative |
| 0.050 | Pos/Neg* | Positive | Positive | Negative | Positive |
| 0.100 | Positive | Positive | Positive | Negative | Positive |
| 0.200 | Positive | Positive | Positive | Negative | Positive |
| 0.500 | Positive | Positive | Positive | Negative | n.t. |
| 1.000 | Positive | Positive | Positive | Positive | n.t. |
| 2.500 | Positive | Positive | Positive | Positive | Positive |
| 5.000 | Positive | Positive | Positive | Positive | n.t. |
| 10.000 | Positive | Positive | Positive | Positive | n.t. |
| 25.000 | Positive | Positive | Positive | Positive | Positive |
| 1.0 mg bov. Hb/g | Negative | Negative | Negative | Positive | Negative |

*One out of three reaction units was positive; 2 out of three reaction units were negative.

As illustrated in Tables 1–3, the assay of the present invention detects the presence of 0.050 mg/g hemoglobin in feces.

EXAMPLE III

Sensitivity of the One-Step Fecal Occult Blood Assay

Samples were prepared by adding various concentrations of human hemoglobin to transport buffer. The samples were tested using the one step fecal occult blood assay of the present invention as described above in connection with Example II. 30 minutes after addition of the sample, each result was judged to be either negative or positive. The samples were tested on 3 different manufacturing lots of the reaction units of the present invention.

The samples were also tested using Hemoccult® SENSA® and OC-Hemodia® according to manufacturer's instructions. The results are shown in Table 4. In addition to the abbreviations used in Tables 1–3, the abbreviations in Table 4 are: "Exp." for expiration date (followed by the date in month/year), and "HuHb" for human hemoglobin. The columns in Tables 4 labeled with "CARDS® O.S.® FOBT" refer to the results obtained with the present invention. The assay of the present invention gave a positive result with samples containing from 0.5–1.0 µg/mL hemoglobin.

TABLE 4

Analytical Sensitivity of CARDS ® O.S. ® FOBT Using Serial Hemoglobin Dilutions

| | REACTION UNIT SKD Hemoccult ® SENSA ® slides Eiken OC-Hemodia ® | | lot #B01032, #B02001, #B04056.2 lot #50929A lot #33020 | Exp. 6/95 Exp. 3/94 | |
|---|---|---|---|---|---|
| HuHb Conc. (µg/mL) | CARDS ® O.S. ® Interpretation Lot #B01032 | CARDS ® O.S. ® Interpretation Lot #B02001 | CARDS ® O.S. ® Interpretation Lot #B04056.2 | Hemoccult ® SENSA ® Interpretation | OC-Hemodia ® Interpretation |
| 1000 | Positive | Positive | Negative | Positive | Positive |
| 500 | Positive | Positive | Positive | Positive | Positive |
| 250 | Positive | Positive | Positive | Positive | Positive |
| 100 | Positive | Positive | Positive | Positive | Positive |
| 50 | Positive | Positive | Positive | Positive | Positive |
| 25 | Positive | Positive | Positive | Positive | Positive |
| 10 | Positive | Positive | Positive | Negative | Positive |
| 5 | Positive | Positive | Positive | Negative | Positive |
| 2 | Positive | Positive | Positive | Negative | Positive |
| 1 | Positive | Positive | Positive | Negative | Positive |
| 0.5 | Negative | Negative | Positive | Negative | Positive |
| 0.1 | Negative | Negative | Negative | Negative | Negative |
| 0.025 | Negative | Negative | Negative | Negative | Negative |
| Transport buffer | Negative | Negative | Negative | Negative | Negative |

Control solutions may be used for the purpose of comparison with assay results or to test reagent viability. For example, a positive control comprising human hemoglobin can be used. A negative control comprising bovine hemoglobin can be used. These controls should be tested on the reaction unit in the same manner as a sample. The controls may be provided in a kit form with any or all of the reagents and assay components disclosed herein.

Although the invention has been described in the context of particular embodiments, it is intended that the scope of coverage of the patent not be limited to those particular embodiments, but be determined by reference to the following claims.

What is claimed is:

1. An analytical device having controlled sensitivity for the detection of the presence of an analyte in a liquid sample, comprising:

an absorbent sample application area having a predetermined amount of a first antibody deposited thereon that binds to said analyte;

one or more wicking materials comprising a plurality of substantially planar zones adjacent one another and in absorbent contact with one another; said zones comprising:

a conjugate zone in fluid communication with said sample application area comprising a first mobilizable conjugate comprising a second antibody that binds to said analyte; and first visually detectable particles bound to said second antibody; and a detection zone comprising a third antibody that binds to said analyte immobilized on said one or more wicking materials, such that when the liquid sample containing said analyte therein is applied to said sampleapplication area, a threshold amount of the analyte is bound to said first antibody and thereby prevented from binding to said second antibody, and the analyte remaining unbound in said liquid sample passes from the sample application area through said conjugate zone where it is bound to said second antibody of the first mobilizable conjugate, and the analyte bound to the first mobilizable conjugate passes through the detection zone where the analyte is bound to said third antibody and the analyte bound to the first mobilizable conjugate is immobilized.

2. The device of claim 1, wherein said visually detectable particles are selected from the group consisting of colored latex particles and a metal sol.

3. The device of claim 1, wherein said visually detectable particles are colored latex particles of diameter from less than about 0.1 µm to about 100 µm.

4. The device of claim 1, wherein said one or more wicking materials is nitrocellulose.

5. The device of claim 1, wherein said first antibody is monoclonal.

6. The device of claim 1, wherein said second antibody is monoclonal.

7. The device of claim 1, wherein said second antibody is the same antibody as said first antibody.

8. The device of claim 1, wherein said first antibody is polyclonal.

9. The device of claim 1, wherein said third antibody is the same antibody as said first antibody.

10. The device of claim 1, wherein said conjugate zone further comprises a second mobilizable conjugate comprising an antigen conjugated to second visually detectable particles, and wherein said one or more wicking materials further comprises a test complete zone, said test complete zone comprising a fourth antibody that binds to said antigen.

11. The device of claim 10, wherein said antigen is goat serum albumin.

12. The device of claim 1, further comprising a negative signal, said negative signal comprising third visually detectable particles immobilized on the one or more wicking materials in said detection zone.

13. The device of claim 12, wherein said third visually detectable particles are immobilized on the one or more wicking materials in a horizontal line, and said third antibody is immobilized on the one or more said wicking materials in a vertical line which crosses said horizontal line.

14. A method for the detection of an analyte in a liquid sample using a device comprising a sample application area having a predetermined amount of a first antibody that binds to said analyte deposited thereon in fluid communication with one or more wicking materials comprising a plurality of substantially planar zones adjacent one another and in absorbent contact with one another; said zones comprising a conjugate zone comprising a mobilizable conjugate comprising a second antibody that binds to said analyte and visually detectable particles; and a detection zone comprising a third antibody that binds to said analyte immobilized on said one or more wicking materials, such that when the liquid sample containing said analyte therein is applied to said sample application area, a threshold amount of the analyte is bound to said first antibody and thereby prevented from binding to said second antibody, and the analyte remaining unbound in said liquid sample passes from the sample application area through said conjugate zone where it is bound to said second antibody of the mobilizable conjugate, and the analyte bound to the mobilizable conjugate passes through the detection zone where the analyte is bound to said third antibody and the analyte bound to the first mobilizable conjugate is immobilized, said method comprising:

applying the liquid sample to the sample application area of the device;

waiting a sufficient time to allow the liquid sample to traverse the sample application area, the conjugate zone and the detection zone; and determining the presence or absence of said analyte in the liquid sample based on the appearance of the detection zone.

15. In a one-step immunochromatographic assay for the detection of the presence of an analyte in a liquid sample involving the interaction of antigens and antibodies on a support layer, wherein one of the reagents used in the assay comprises a mobilizable conjugate comprising a first antibody that binds to said analyte bound to a visually detectable particle, and another reagent comprises a second antibody that binds to said analyte immobilized in a defined zone on said support layer, wherein the improvement comprises contacting said liquid sample with a predetermined amount of an antibody that binds to said analyte and thereby prevents said analyte from binding to said first and second antibodies, prior to contacting said liquid sample with said first and second antibodies, said antibody being deposited on a defined application zone on said support layer.

16. An analytical device having controlled sensitivity for the detection of the presence of blood in a sample of human feces containing human hemoglobin, comprising:

an absorbent sample application area having a predetermined amount of a first antibody deposited thereon that binds to said human hemoglobin;

one or more wicking materials comprising a plurality of substantially planar zones adjacent one another and in absorbent contact with one another; said zones comprising a conjugate zone in fluid communication with the sample application area, comprising a first mobilizable conjugate comprising a second antibody that binds to said human hemoglobin; and first visually detectable particles bound to said second antibody; and a detection zone comprising a third antibody that binds to said human hemoglobin immobilized on said one or more wicking materials; such that when the sample of feces containing said human hemoglobin therein is suspended in a buffer to make a liquid sample of feces and said liquid sample is applied to said sample application area, a threshold amount of the human hemoglobin is bound to said first antibody and thereby prevented from binding to said second antibody, and the human hemoglobin remaining unbound in said liquid sample passes from the sample application area through said conjugate zone where it is bound to said second antibody of the first mobilizable conjugate, and the human hemoglobin bound to the first mobilizable conjugate passes through the detection zone where the human hemoglobin is bound to said third antibody and the human hemoglobin bound to the first mobilizable conjugate is immobilized, producing a detectable signal.

17. The device of claim 16, wherein said visually detectable particles are selected from the group consisting of colored latex particles and a metal sol.

18. The device of claim 16, wherein said visually detectable particles are colored latex particles of diameter from less than about 0.1 μm to about 100 μm.

19. The device of claim 16, wherein said one or more wicking materials is nitrocellulose.

20. The device of claim 16, wherein said first antibody is monoclonal.

21. The device of claim 16, wherein said second antibody is monoclonal.

22. The device of claim 16, wherein said second antibody is the same antibody as said first antibody.

23. The device of claim 16, wherein said first antibody is polyclonal.

24. The device of claim 16, wherein said third antibody is the same antibody as said first antibody.

25. The device of claim 16, wherein said conjugate zone further comprises a second mobilizable conjugate comprising an antigen conjugated to second visually detectable particles, and wherein said one or more wicking materials further comprises a test complete zone, said test complete zone comprising a fourth antibody that binds to said antigen.

26. The device of claim 25, wherein said antigen is goat serum albumin.

27. The device of claim 16, further comprising a negative signal, said negative signal comprising third visually detectable particles immobilized on the one or more wicking materials in said detection zone.

28. The device of claim 27, wherein said third visually detectable particles are immobilized on the one or more wicking materials in a horizontal line, and said third antibody is immobilized on the one or more wicking materials in a vertical line which crosses said horizontal line.

29. A method for the detection of blood in a sample of feces containing hemoglobin, using a device comprising a sample application area having a predetermined amount of a first antibody deposited thereon that binds to said hemoglobin; in fluid communication with one or more wicking materials comprising a plurality of substantially planar zones adjacent one another and in absorbent contact with one another; said zones comprising a conjugate zone comprising a mobilizable conjugate comprising a second antibody that binds to said hemoglobin and visually detectable particles; and a detection zone comprising a third antibody that binds to said hemoglobin immobilized on said one or more wicking materials, such that when the sample of feces containing said hemoglobin therein is suspended in a buffer to make a liquid sample of feces and said liquid sample is applied to said sample application area, a threshold amount of the hemoglobin is bound to said first antibody and thereby prevented from binding to said second antibody, and the hemoglobin remaining unbound in said liquid sample passes from the sample application area through said conjugate zone where it is bound to said second antibody of the mobilizable conjugate, and the hemoglobin bound to the mobilizable conjugate passes through the detection zone where the hemoglobin is bound to said third antibody and the hemoglobin bound to the mobilizable conjugate is immobilized, producing a detectable signal, said method comprising:

suspending the sample of feces into the buffer to make the liquid sample of feces;

applying the liquid sample of feces to the sample application area of the device;

waiting a sufficient time to allow the liquid sample to traverse the sample application zone, the conjugate zone and the detection zone; and determining the presence or absence of the hemoglobin in the liquid sample based on the appearance of the detection zone to detect said blood in said sample of feces.

* * * * *